United States Patent [19]

Brinker et al.

[11] Patent Number: 5,268,182

[45] Date of Patent: Dec. 7, 1993

[54] SUSTAINED-RELEASE DRUG DOSAGE UNITS OF TERAZOSIN

[75] Inventors: Dale R. Brinker, Antioch; Enrique D. Eveline, Waukegan, both of Ill.

[73] Assignee: Abbott Laboratories, Abbott Park, Ill.

[21] Appl. No.: 931,188

[22] Filed: Aug. 14, 1992

Related U.S. Application Data

[60] Division of Ser. No. 709,952, Jun. 4, 1991, Pat. No. 5,169,642, which is a continuation-in-part of Ser. No. 605,152, Nov. 2, 1990, abandoned, which is a continuation-in-part of Ser. No. 444,458, Dec. 1, 1989, abandoned, which is a continuation-in-part of Ser. No. 353,809, May 22, 1989, abandoned, which is a continuation-in-part of Ser. No. 211,495, Jun. 24, 1988, abandoned.

[51] Int. Cl.$^5$ .......................... A61K 9/14; A61K 9/26; A61K 31/505

[52] U.S. Cl. ..................... 424/488; 424/468; 424/469; 424/470; 424/486; 424/494; 424/495; 424/497; 424/498; 424/499; 424/501; 424/502; 514/254; 514/929

[58] Field of Search .............. 424/488, 470, 468, 469, 424/490, 486, 499, 494, 495, 497, 498

[56] References Cited

U.S. PATENT DOCUMENTS

| | | | |
|---|---|---|---|
| 4,138,475 | 2/1979 | McAinsh et al. | 424/459 |
| 4,199,560 | 4/1980 | Gyarmati et al. | 424/19 |
| 4,252,786 | 2/1981 | Weiss et al. | 424/19 |
| 4,351,825 | 9/1982 | Sothmann et al. | 424/19 |
| 4,555,399 | 11/1985 | Hsiao et al. | 424/465 |
| 4,572,833 | 2/1986 | Pedersen et al. | 424/20 |
| 4,713,248 | 12/1987 | Kjornaes et al. | 424/468 |
| 4,716,041 | 12/1987 | Kjornaes et al. | 424/468 |
| 4,748,023 | 5/1988 | Tamas et al. | 424/465 |
| 4,756,911 | 7/1988 | Drost et al. | 424/468 |
| 4,772,475 | 9/1988 | Fukui et al. | 424/468 |
| 4,786,506 | 11/1988 | Fontanelli | 424/470 |
| 4,800,087 | 1/1989 | Mehta et al. | 424/497 |
| 4,828,840 | 5/1989 | Sakamoto et al. | 424/474 |
| 4,874,614 | 10/1989 | Becker et al. | 424/465 |
| 4,913,906 | 4/1990 | Friedman et al. | 424/499 |
| 4,925,675 | 5/1990 | Giannini et al. | 424/469 |
| 4,942,040 | 7/1990 | Ragnarsson et al. | 424/486 |
| 4,957,745 | 9/1990 | Jonsson et al. | 424/461 |

FOREIGN PATENT DOCUMENTS

| | | |
|---|---|---|
| 24727/88 | 5/1989 | Australia . |
| 092060 | 10/1983 | European Pat. Off. . |
| 133110 | 2/1985 | European Pat. Off. . |
| 347748 | 12/1989 | European Pat. Off. . |
| 385846 | 5/1990 | European Pat. Off. . |

Primary Examiner—Thurman K. Page
Assistant Examiner—James M. Spear
Attorney, Agent, or Firm—Steven R. Crowley

[57] ABSTRACT

A sustained-release coating composition is described that contains an ethylcellulose and/or a methacrylic methylester together with a plasticizer and a detackifying agent. Sized drug granules are coated with this composition and then mixed with a polymeric composition containing at least one viscosity agent and formed into drug dosage units for the administration and sustained release of the drug in a patient.

The sustained-release drug dosage units described produce a continuous, slow release of the drug at a therapeutically effective dosage level when administered to a patient.

9 Claims, No Drawings

SUSTAINED-RELEASE DRUG DOSAGE UNITS OF TERAZOSIN

This is a division of U.S. patent application Ser. No. 709,952, filed Jun. 4, 1991, now U.S. Pat. No. 5,169,642, a continuation-in-part of U.S. patent application Ser. No. 605,152, filed Nov. 2, 1990, (abandoned) which is a continuation-in-part of U.S patent application Ser. No. 444,458, filed Dec. 1, 1989,(abandoned) which is a continuation-in-part of U.S. patent application Ser. No. 353,809, filed May 22, 1989 (abandoned), which is a continuation-in-part of U.S. patent application Ser. No. 211,495, filed Jun. 24, 1988 (abandoned).

TECHNICAL FIELD

The present invention relates to sustained-release drug dosage units. Compositions and methods for preparing sustained-release dosage units are described.

BACKGROUND OF THE INVENTION

The use of sustained-release drug dosage units for the oral administration of drugs to a patient has several therapeutic advantages. A therapeutically effective systemic level of a drug can be maintained over an extended time period without the necessity of multiple daily drug administration. Some drugs are toxic or otherwise deleterious in high concentrations, and thus require multiple administration of low-level amounts of these drugs to patients. Such administration results in a bolus rise in drug concentration initially, above the most effective therapeutic level, and a concomitant decrease over time below this level, producing a high-low fluctuation in blood levels of the drug. Sustained-release dosage forms overcome this problem by releasing the drug in small amounts throughout a predetermined time period and thus maintaining the drug level in the blood within a narrow therapeutically effective range as the rate of drug release and systemic drug removal are maintained in balance.

Numerous methods and compositions for preparing controlled-release drug compositions are known, and include those described in U.S. Pat. No. 4,572,833 to Pedersen, et al.; U.S. Pat. Nos. 4,713,248 and 4,716,041 to Kjornaes, et al; U.S. Pat. No. 4,772,475 to Fukui, et al.; U.S. Pat. No. 4,756,911 to Drost, et al.; U.S. Pat. No. 4,786,506 to Fontanelli; U.S. Pat. No. 4,351,825 to Southman, et al; U.S. Pat. No.4,252,786 to Weiss, et al.; U.S. Pat. No. 4,199,560 to Gyarmati, et al; and Colombo, et al., European Patent Application No. EP0092060.

SUMMARY OF THE INVENTION

The present invention is directed to a sustained-release drug coating composition, sustained-release coated drug granules, sustained-release drug dosage units and methods for the preparation and administration of a sustained-release drug dosage unit.

More particularly, the present invention is directed to drug granules coated with a composition which slows drug release. These coated drug granules are mixed with polymeric materials to form a dosage unit that further slows release of the drug. The resulting composition provides a continuous slow release of a therapeutically effective level of drug in the patient.

The sustained-release drug coating composition of the present invention comprises about 2 to about 20 weight percent (w/v) of an ethylcellulose and/or a methacrylic methylester, about 0.1 to about 5.0 weight percent (w/v) of a plasticizer and about 0.5 to about 20 weight percent (w/v) of a detackifying agent.

A drug dosage unit of the present invention contains sustained-release coated drug granules together with at least one viscosity agent such as methylcellulose, hydroxypropylmethylcellulose, povidone, hydroxypropylcellulose, and the like. The dosage unit is preferably a tablet formed by compression of this mixture.

A method of treatment of the present invention comprises orally administering a drug dosage unit of the present invention to a patient in need of such treatment.

The present invention is also directed to a method for the preparation of a sustained-release drug dosage unit. In this method, a drug is first admixed with a detackifying agent such as silica gel and wetted with a solvent such as ethanol with further mixing to form drug granules. The drug granules are then dried and sized, such as by sifting through screens, to obtain granules of a desired size; larger granules are then milled and sized to produce more drug granules of the desired size. The appropriately sized granules are then admixed with a sustained-release drug coating composition of the present invention to produce coated drug granules. The coated drug granules are then mixed with at least one viscosity agent of the present invention and formed into sustained-release drug dosage units such as tablets.

DESCRIPTION OF PREFERRED EMBODIMENTS

The present invention is directed to the sustained release of a drug over a predetermined time period following administration to a patient. A drug is formulated into granules and then coated with a coating composition that contains an ethylcellulose and/or a methacrylic methylester together with plasticizer and a detackifying agent dissolved or dispersed in a solvent such as ethanol and/or acetone.

As used herein, the term "coating composition" refers to a mixture of designated compounds that when applied to granules of a drug produces an insoluble coating through which the drug is slowly released.

As used herein, the terms "an ethylcellulose" and "a methacrylic methylester" refer to both substituted and unsubstituted forms of ethylcellulose and methacrylic methylester, respectively, and include ethylcellulose, hydroxypropylethylcellulose, methacrylic methylester, polymethylmethacrylate, and the like.

As used herein, the term "plasticizer" refers to a component of the coating composition that has a low vapor pressure and whose presence in the composition modifies the flexibility and diffusion properties of the coating composition.

As used herein, the term "detackifying agent" refers to a compound whose presence in the coating composition reduces the stickiness or adhesion of the coated drug granules.

Plasticizers useful in the coating composition can include castor oil, propylene glycol, polyethylene glycol, acetyl triethyl citrate, acetyl tributyl citrate, triethyl citrate, tributyl citrate, and the like. Plasticizers are present in the coating composition of the present invention at a concentration of about 0.1 to about 5.0 weight percent (w/v) of the total weight of the composition.

Detackifying agents useful in the present invention include magnesium stearate, talc, titanium dioxide, silica gel, and the like. The detackifying agent is present in the coating composition of the present invention at a concentration of about 0.5 to about 20 weight percent (w/v) of the total weight of the composition.

Drugs useful in the present invention are orally administerable drugs and preferably include divalproex sodium and valproic acid, its salts or derivatives thereof. Other drugs useful in the present invention include terazosin (2-[4-[(tetrahydro-2-furanyl)carbonyl]-1-piperazinyl]-6,7-dimethoxy-4-quinazolinamine), its salts, hydrates or derivatives thereof. Terazosin, its salts, hydrates or derivatives thereof can be in the form of a racemic mixture or the individual R(+)- or S(−)- enantiomer.

Derivatives of valproic acid include amides and esters thereof. Esters of valproic acid include the 2-propylpentanol-di-n-propylacetate and glycerol tri(dipropylacetate).

Salts of valproic acid refer to salts with alkali metals or alkaline earth metals, such as sodium, potassium, calcium or magnesium or with organic bases and the like.

Salts of terazosin refer to the relatively non-toxic, inorganic and organic acid addition salts of the compound of terazosin. These salts can be prepared in situ during the final isolation and purification of the compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, tosylate, glucoheptonate, lactobionate, laurylsulphonate salts and the like. (See, for example S. M. Berge, et al., "Pharmaceutical Salts," *J. Pharm. Sci.*, 66: 1-19 (1977) which is incorporated herein by reference.) The particularly preferred salt of hytrin is the hydrochloride.

In a preferred embodiment, granules of divalproex sodium or terazosin hydrochloride dihydrate are coated with a composition containing ethylcellulose, castor oil and magnesium stearate in a solvent mixture such as ethanol and acetone.

In a particularly preferred embodiment, a sustained-release drug particle composition of the present invention comprises about 62 weight percent divalproex sodium, about 2.6 weight percent silica gel, about 11.6 weight percent ethylcellulose, about 1.9 weight percent castor oil, about 11.6 weight percent magnesium stearate, from about 0.04 to about 0.09 weight percent of an edible dye, about 1.0 weight percent povidone and about 9.7 weight percent microcrystalline cellulose.

In another particularly preferred embodiment, a sustained-release drug particle composition of the present invention comprises about 12.9 weight percent terazosin monohydrochloride dihydrate, about 5.5 weight percent povidone, about 53.6 weight percent sugar spheres, about 8.0 weight percent ethylcellulose, about 1.3 weight percent castor oil, about 8.0 weight percent magnesium stearate and about 10.7 weight percent microcrystalline cellulose.

The sustained-release coated drug granules of the present invention are formed into drug dosage units, such as tablets, by admixing them together with at least one viscosity agent, and preferably with two viscosity agents, prior to forming the composition into tablets. Illustrative viscosity agents include methylcellulose, hydroxypropylmethylcellulose, povidone and hydroxypropylcellulose.

As used herein, the term "drug dosage unit" refers to a dosage form that is capable of being orally administered to produce a sustained release of a drug therefrom. Illustrative drug dosage units include tablets, capsules and lozenges.

As used herein, the term "viscosity agent" refers to an ingredient of a drug dosage unit which forms an insoluble or non-disintegrating polymeric matrix in which the coated drug granules of the present invention are enclosed, and from which the drug is slowly released.

A preferred drug dosage unit of the present invention contains about 2.0 to about 80 weight percent of sustained-release coated drug granules, about 0 to about 35 weight percent of calcium phosphate, about 2 to about 30 weight percent of a first viscosity agent and about 0 to about 30 weight percent of a second viscosity agent.

In a particularly preferred embodiment, the drug granules contain divalproex sodium, and the dosage unit contains from about 63 to about 65 weight percent of sustained-release coated granules of divalproex sodium, from about 3.5 to about 4.5 weight percent of methylcellulose, from about 14.2 to about 14.6 weight percent of hydroxypropylmethylcellulose, from about 14.2 to abut 14.6 weight percent of dibasic calcium phosphate, from about 0.7 to about 0.8 weight percent of stearic acid and from about 1.5 to about 2.2 weight percent of talc.

In another particularly preferred embodiment, the drug granules contain terazosin monohydrochloride dihydrate, and the dosage unit contains from about 2.6 to about 26.4 weight percent of sustained-release coated granules of terazosin hydrochloride dihydrate, about 2.5 weight percent of methylcellulose, about 10.5 weight percent of hydroxypropylmethylcellulose, about 34.0 weight percent of dibasic calcium phosphate, about 1.1 weight percent of stearic acid and about 1.9 weight percent of talc.

The present invention is also directed to a method of treatment in which a sustained-release drug dosage unit is administered to a patient in need of such treatment for the sustained release of a drug such as divalproex sodium or terazosin. In this method, a drug dosage unit of the present invention is orally administered to a patient, to release the drug systemically over a period of about 10 to about 12 hours.

A drug dosage unit of the present invention is prepared by admixing a drug, such as divalproex sodium or valproic acid, it salts or derivatives thereof, or terazosin, its salts, hydrates or derivatives thereof, with a detackifying agent such as silica gel in a solvent, such as ethanol, to produce drug granules. The drug granules are then dried, such as by warm air, and sized, such as by sifting through screens, to obtain granules of a desired size. Large granules are further milled and sized to obtain granules of the desired size. These granules are then mixed with a coating composition of the present invention to produce coated granules, which are then mixed with a composition containing at least one viscosity agent, and then formed into an appropriate drug dosage unit, such as tablets.

As used herein, the term "sizing screen" refers to a screen having openings of a definite specified size over which a mixture of solid particles, such as drug granules, is placed to fractionate the particles by size. Particles smaller than the openings fall through the screen and are collected. Particles larger than the specified size of the openings are retained and separated from the smaller particles. In the present invention, such retained particles are further milled to produce smaller particles and then placed over the screen to collect additional particles that can pass through the screen openings.

In a preferred embodiment of this method, granules of divalproex sodium are mixed with silica gel and suspended in ethanol. The granules are then dried in warm air and passed through sizing screens to produce granules smaller than a selected size. The sized granules are then mixed with a coating composition comprising ethycellulose, castor oil, magnesium stearate, acetone and ethanol. The coated drug granules are then sifted through another screen to obtain desired-size coated granules which are then blended together with methylcellulose, hydroxypropylmethylcellulose, calcium phosphate, stearic acid and talc and compressed into tablets.

In another preferred embodiment of this method, terazosin hydrochloride dihydrate and povidone in ethanol are coated on sugar spheres. The terazsosin particles are then mixed with a coating composition comprising ethylcellulose, castor oil, magnesium stearate, ethanol and acetone. The coated drug particles are sifted through a sizing screen and blended together with methylcellulose, hydroxylpropylmethylcellulose, calcium phosphate, stearic acid and talc and compressed into tablets The following examples will serve to further illustrate the invention.

EXAMPLE 1

Divalproex Sodium Tablets

1A Preparation of Granular Drug Particles

Divalproex sodium (19.2 kg) was mixed with pharmaceutical-grade silica gel (800 g, Syloid 244) and the mixture was milled in a Fitzmill at medium speed with knives forward through a 2A band, for 5 minutes.

The milled mixture was then placed in a granulation mixer, and ethanol (1.2 kg, 200 proof) was added during mixing at low speed until the mixture was granular (about 3 minutes). The granular mixture was removed and dried in an Aeromatic Fluid Bed Dryer at 45° C. to 50° C. The granulated mixture was then sifted through a 12-mesh and then a 24-mesh screen. The material that passed through the 12-mesh screen and that was retained on the 24-mesh screen was collected. The material retained on the 12-mesh screen was re-milled in a Fitzmill at medium speed through a 2A band and then resifted through 12-mesh and 24-mesh screens.

1B Drug Granule Coating Composition

Ethanol (12 liters, 200 proof) and acetone (40 liters) were mixed together. Triethyl citrate (600 g) and ethylcellulose (3600 g) were slowly added to the mixture, and mixing continued to produce a clear solution. Magnesium stearate (3600 g) and blue dye (12 g, FD and C No. 2) were added with mixing. Acetone was then added to bring the volume to 60 liters.

1C Compression Enhancing Coating Composition

Ethanol (25 liters, 200 proof) was combined with povidone (300 g) and mixed for about one hour to produce a clear solution. Microcrystalline cellulose (3000 g) was added to the solution with continued mixing. Ethanol (200 proof) was then added to bring the volume to 30 liters.

1C Coating of Drug Granules

The coating composition of EXAMPLE 1B was applied to the drug granules (12-24 mesh) of EXAMPLE 1A at a concentration of 3 liters of coating composition per 1 kg of drug granules. The compression coating composition of EXAMPLE 1C (1.5 liters per kg of particles) was added to the mixture. The particles were dried by fluidizing without spraying for 30 minutes to produce a loss on drying (L.O.D.) of not more than 0.5 percent at 110° C.

The coated particles were collected and sifted through a 10-mesh screen and the coated particles that passed through the screen were collected.

1E Preparation of Tablets

The coated particles (4.2 kg) obtained in EXAMPLE 1D were combined with methylcellulose (250 g, 15 cps), hydroxypropylmethylcellulose (950 g, USP 2910, 100 cps), calcium phosphate (950 g), stearic acid (50 g) and talc (100 g), and mixed in a blender. The blended mixture was then compressed into tablets.

EXAMPLE 2

Divalproex Sodium Tablets

2A Preparation of Granular Drug Particles

Divalproex sodium (1440 kg) was mixed with pharmaceutical-grade silica gel (60 kg, Syloid 244) and the mixture was milled in a Fitzmill at medium speed with knives forward through a 2A band, for 5 minutes.

The milled mixture was then placed in a granulation mixer with ethanol (100 liters, 200 proof) and mixed at low speed until the mixture was granular. The granular mixture was removed and dried in an Aeromatic Fluid Bed Dryer at 45° C. to 50° C. to produce a loss on drying (L.O.D.) of not more than 0.5 percent. The granulated mixture was then sifted through a 12-mesh and then a 24-mesh screen. The material that passed through the 12-mesh screen and that was retained on the 24-mesh screen was collected. The material retained on the 12-mesh screen was re-milled in a Fitzmill at medium speed through a 2A band and then resifted through 12-mesh and 24-mesh screens.

2B Drug Granule Coating Composition

Ethanol (150 liters, 200 proof) and acetone (450 liters) were mixed together. Castor oil (7.5 kg) and ethylcellulose (45 kg) were slowly added to the mixture, and mixing continued to produce a clear solution. Magnesium stearate (45 kg) and blue dye (300 g, FD and C No. 2) and yellow dye (56.25 g, D and C No. 10) were added with mixing. Acetone was then added to bring the volume to 750 liters.

2C Compression Enhancing Coating Composition

Ethanol (280 liters, 200 proof) was combined with povidone (7.6 kg) and mixed for about one hour to produce a clear solution. Microcrystalline cellulose (76 kg) was added to the solution with continued mixing. Ethanol (200 proof) was then added to bring the volume to 380 liters.

2D Coating of Drug Granules

The coating composition of EXAMPLE 2B was applied to the drug granules (12-24 mesh) of EXAMPLE 2A at a concentration of 3 liters of coating composition per 1 kg of drug granules. (Inlet Air Temp.: 50° C.; Relative Humidity: 0%; Chamber Pressure: −10 mm H2O; Atomization Air Pressure; 65 PSIG; Process Air Flow Rate: 4000 SCMH; Solution Flow Rate: 310 ml/minute/nozzle). The compression coating composition of EXAMPLE 2C (0.75 liters per kg of particles) was added to the mixture. (Inlet Air Temp.: 48°-50° C.; Relative Humidity: 0%; Chamber Pressure: −10 mm H2O; Atomization Air Pressure: 40 PSIG; Process Air Flow Rate: 6000 SCMH; Solution Flow Rate: 350 ml/minute/nozzle). The particles were dried by fluidizing without spraying for 20 minutes to produce a loss on drying (L.O.D.) of not more than 0.5 percent at 110° C.

The coated particles were collected and sifted through a 10-mesh screen and the coated particles that passed through the screen were collected.

2E Preparation of Tablets

The coated particles (98.04 kg) obtained in EXAMPLE 2D were combined with methylcellulose (6.75 kg, 15 cps), hydroxypropylmethylcellulose (22.5 kg, USP 2208, 100 cps), calcium phosphate (22.5 kg), stearic acid (1.125 kg) and talc (3.375 kg), and mixed in a blender. The blended mixture was then compressed into tablets.

EXAMPLE 3

Bioavailability Study

Drug tablets were administered to 15 adult males under fasting and non-fasting conditions.

Two formulations of divalproex sodium were utilized to determine bioavailability data.

Formulation A was the controlled-release dosage form of the present invention containing 500 mg valproic acid equivalent per tablet and prepared according to the general procedure of Example 2.

Formulation B was an enteric coated tablet (Depakote ®) containing 250 mg valproic acid equivalent per tablet.

A single dose of 1000 mg valproic acid equivalent (two tablets of Formulation A, or four tablets of Formulation B) was administered to each subject. Each subject was a healthy adult male between 18 and 40 years of age. Formulation A was administered under fasting and non-fasting conditions.

The subjects were housed and supervised for four and one-half days in each study period, from a minimum of 12 hours prior to administration of the drug dose through the 72-hour blood collection.

The subjects abstained from all food and beverage except for scheduled meals and water during the study period. Under non-fasting conditions, the subjects were served a meal one-half hour prior to administering a dose of Formulation A. Under fasting conditions, the subjects were served a meal 2 hours after administration of doses of Formulations A and B, respectively. All subjects received a meal 6 hours after drug administration and, thereafter, at 11 hours, 24.5 hours, 28 hours, and 34 hours after drug administration. Seven-milliliter blood samples were collected in heparinized tubes from each subject prior to drug administration (0 hour) and at 1, 2, 3, 4, 6, 8, 10, 12, 15, 18, 24, 30, 36, 48, 60 and 72 hours after drug administration, and stored at 0° C. until separation into plasma (within 3 hours after collection and plasma was stored at −10° C.).

The results obtained are shown in TABLE I.

TABLE I

| Time (hours) | Plasma Valproic Acid Concentration (μg/ml) | | |
|---|---|---|---|
| | Formulation A (fasting) | Formulation A (non-fasting) | Formulation B (fasting) |
| 0 | 0.0 (0.1) | 0.0 (0.0) | 0.0 (0.1) |
| 1 | 3.9 (1.2) | 1.4 (0.9) | 1.4 (2.6) |
| 2 | 12.3 (3.1) | 12.8 (21.9) | 47.2 (36.9) |
| 3 | 21.3 (4.7) | 20.6 (23.8) | 72.0 (31.2) |
| 4 | 36.1 (23.1) | 28.4 (19.0) | 60.5 (30.5) |
| 6 | 35.2 (6.7) | 43.1 (11.2) | 59.4 (19.5) |
| 8 | 47.1 (8.2) | 49.4 (7.7) | 58.7 (7.4) |
| 10 | 54.3 (7.4) | 55.7 (9.9) | 52.2 (6.7) |
| 12 | 60.1 (9.0) | 58.0 (7.7) | 50.1 (13.0) |
| 15 | 52.0 (7.9) | 51.0 (7.0) | 41.5 (10.6) |
| 18 | 44.8 (6.9) | 42.9 (7.8) | 34.3 (9.6) |
| 24 | 34.3 (6.3) | 33.9 (5.8) | 27.1 (8.9) |
| 30 | 23.4 (6.4) | 22.6 (4.7) | 18.3 (5.7) |
| 36 | 17.5 (4.4) | 16.7 (4.3) | 13.6 (4.6) |
| 48 | 10.0 (3.5) | 9.7 (3.4) | 8.4 (3.4) |
| 60 | 5.6 (2.3) | 5.5 (2.2) | 4.8 (2.4) |
| 72 | 3.7 (1.8) | 3.5 (1.8) | 3.1 (1.9) |
| $T_{max}$ | 10.9 (3.4) | 11.0 (2.7) | 4.3 (3.3) |
| $C_{max}$ | 65.1 (11.9) | 63.7 (12.6) | 87.0 (9.5) |
| AUC | 1585.0 (278.8) | 1557.6 (244.0) | 1527.9 (264.6) |

$T_{max}$ = Time of peak concentration (hours).
$C_{max}$ = Peak concentration (μg/ml).
AUC = Area under Plasma Concentration - Time Curve, 0 to 72 hours (μg × hr/ml).

The values in parentheses represent the standard deviation.

The results show that the controlled-release dosage form of the present invention had a lower $C_{max}$ in plasma in both fasting and non-fasting subjects than the enteric coated tablets, and maintained a higher plasma concentration of valproic acid over time.

EXAMPLE 4

Terazosin Hydrochloride Dihydrate Tablets

4A Preparation of Drug Particles

Terazosin hydrochloride dihydrate (48.0 kg) was mixed with povidone (16.0 kg) and ethanol (300 liters, 200 proof). After mixing, ethanol (200 proof) was added to bring the final volume to 400 liters.

200 kg of sugar spheres (40-50 mesh) were coated with the above-mentioned solution of terazosin. (Inlet Air Temp.: 52° C.; Relative Humidity: 15%; Chamber Pressure: −10 mm H2O; Atomization Air Pressure; 65 PSIG; Process Air Flow Rate: 3000-3500 SCMH; Solution Flow Rate: 200-215 ml/minute/nozzle).

4B Drug Particle Coating Composition

Ethanol (100 liters, 200 proof) and acetone (300 liters) were mixed together. Ethylcelluose (30 kg) and castor oil (5.0 kg) were slowly added to the mixture and mixing continued to obtain a solution. Magnesium stearate (30 kg) was added with mixing and acetone was then added to bring the final volume to 500 liters.

4C Compression Enhancing Coating Composition

Ethanol (140 liters, 200 proof) was combined with povidone (4.0 kg) and mixed for about 15 minutes to obtain a clear solution. Microcrystalline cellulose (40.0 kg) was added to the solution with continued mixing. Ethanol (200 proof) was added to bring the final volume to 200 liters.

4D Coating of Drug Particles

The drug particles of Example 4A were coated with the particle coating composition of Example 4B (2.5 liters per kg of nonpareils). (Inlet Air Temp.: 48° C.;

Relative Humidity: 15%; Chamber Pressure: −10 mm $H_2O$; Atomization Air Pressure; 65 PSIG; Process Air Flow Rate: 3600 SCMH; Solution Flow Rate: 200–220 ml/minute/nozzle). The coated particles were dried by fluidizing without spraying for 20 minutes. The dried coated particles were sifted through a 20/60 mesh sifter.

The sifted particles were then coated with the compression enhancing coating composition of Example 4C (1.0 liters per kg of nonpareils). (Inlet Air Temp.: 50° C.; Relative Humidity: 15%; Chamber Pressure: −10 mm $H_2O$; Atomization Air Pressure; 40 PSIG; Process Air Flow Rate: 3600 SCMH; Solution Flow Rate: 180 ml/minute/nozzle). The coated particles were dried by fluidizing without spraying for 20 minutes to produce a loss on drying (L.O.D.) of not more than 1.5%. The dried coated particles were sifted through a 20/60 mesh sifter. The particles that passed through the 20 mesh screen but that did not pass through the 60 mesh screen were collected.

4E Placebo Particle Coating Composition

Ethanol (200 liters, 200 proof) and acetone (600 liters) were mixed together. Ethylcellulose (60 kg) and castor oil (10 kg) were slowly added to the mixture and mixing continued to obtain a solution. Magnesium stearate (60 kg) was added with mixing and acetone was added to bring the final volume to 1000 liters.

4F Compression Enhancing Coating Composition

Ethanol (300 liters, 200 proof) was combined with povidone (8.0 kg) and mixed for about 15 minutes to obtain a clear solution. Microcrystalline cellulose (80 kg) was added to the solution with continued mixing. Ethanol (200 proof) was added to bring the final volume to 400 liters.

4G Coating of Placebo Particles 300 kg of sugar spheres (40–50 mesh) were coated with the particle coating composition of Example 4E (500 liters) (Inlet Air Temp.: 48°–50° C.; Relative Humidity: 30%; Chamber Pressure: −10 mm $H_2O$; Atomization Air Pressure; 65 PSIG; Process Air Flow Rate: 3500–4000 SCMH; Solution Flow Rate: 310 ml/minute/nozzle). The coated particles were dried by fluidizing without spraying for 15 minutes. The dried coated particles were sifted through a 20/60 mesh sifter.

The sifted particles were then coated with 200 liters of the compression enhancing coating of Example 4F. (Inlet Air Temp.: 50° C.; Relative Humidity: 30%; Chamber Pressure: −10 mm $H_2O$; Atomization Air Pressure; 40 PSIG; Process Air Flow Rate: 4500 SCMH; Solution Flow Rate: 200 ml/minute/nozzle). The coated particles were dried by fluidizing without spraying for 20 minutes to produce a loss on drying (L.O.D.) of not more than 1.5%. The dried coated particles were sifted through a 20/60 mesh sifter. The particles that passed through the 20 mesh screen but that did not pass through the 60 mesh screen were collected.

4H Preparation of Tablets

Methylcellulose (0.875 kg), hydroxypropyl methylcellulose (3.675 kg), calcium phosphate (11.9 kg), stearic acid (0.4 kg) and talc (0.65 kg) were mixed using a Fitzmill at high speed with knives forward through a 1-A band.

The mixture was charged into a blender along with the coated terazosin particles of Example 4D (2.066 kg) and the coated placebo particles of Example 4G (15.434 kg) and blended for 10 minutes. The blended mixture was then compressed into tablets.

EXAMPLE 5

Preparation of
R(+)-2-[4-[(tetrahydro-2-furanyl)carbonyl]-1-piperazinyl]-6,7-dimethoxy-4-quinazolinamine Step 1—Preparation of R(+)-tetrahydrofuroic acid Using the procedure detailed in *Can. J. Chem.*, 61:1383–1386 (1983), racemic tetrahydro-2-furoic acid was first converted to a mixture of the diastereomeric brucine salts by reaction with (−)-brucine in ethyl acetate. The crude brucine salt of R(+)-tetrahydro-2-furoic acid which first precipitated had a melting point of 191°–197° C. and an optical rotation $[\alpha]_D^{23} = -7.86°$ (C=1, methanol). The material was recrystallized three times from ethyl acetate to yield material melting at 200°–203° C. and having an optical rotation $[\alpha]_D^{23°}$ C. = −4.8° (C=1, methanol) (literature $[\alpha]_D = -5.8°$ (C=1, methanol)).

The salt was acidified to recover R(+)-tetrahydro-2-furoic acid, b.p. 57°–58° C. at 0.1 mm Hg, refractive index, $\eta_D^{25} = 1.4953$, optical rotation $[\alpha]_D^{22°}$ C. = +33.37° (C=1, chloroform) (literature value $[\alpha]_D = +30.4°$ (C=1, chloroform).

Step 2—Preparation of
R(+)-2-[4-[(tetrahydro-2-furanyl)carbonyl]-1-piperazinyl]-6,7-dimethoxy-4-quinazolinamine R(+)-Tetrahydro-2-furoic acid was dissolved in tetrahydrofuran and 2.0 g (0.017 mole) dicyclohexylcarbodiimide was added followed by 3.50 g (0.017 mole) N-hydroxysuccinimide. The mixture was stirred overnight at room temperature. The precipitated dicyclohexylurea which formed was collected by filtration and the residue washed with a small amount of tetrahydrofuran. The solid was discarded and the washings added to the filtrate.

To the filtrate were added a solution of 4.91 g (0.017 mole) of 4-amino-6,7-dimethoxy-2-piperazinyl-4-quinazoline in tetrahydrofuran. The resulting mixture was stirred overnight at room temperature. The solid which had precipitated was collected by filtration and washed several times with tetrahydrofuran. The washings were combined with the filtrate which was evaporated to dryness. The residual solid was taken up in a 5/1 mixture of methylene chloride/methanol and the resulting mixture distilled to remove the methylene chloride. The removed methylene chloride was replaced by an equal volume of methanol, at which point the product began to crystallize from solution. The solution was allowed to cool to room temperature and stand for several hours, yielding R(+)-2-[4-[(tetrahydro-2-furanyl)carbonyl]-1-piperazinyl]- 6,7-dimethoxy-4-quinazolinamine, m.p. 272°–274° C., optical rotation $[\alpha]_D^{22°}$ C. = 34.83° (C=1, 3N hydrochloric acid).

EXAMPLE 6

Preparation of
R(+)-2-[4-[(tetrahydro-2-furanyl)carbonyl]-1-piperazinyl]-6,7-dimethoxy-4-quinazolinamine, hydrochloride salt dihydrate The hydrochloride salt dihydrate was prepared by heating an ethanol solution of R(+)-2-[4-[(tetrahydro-2-furanyl)carbonyl]-1-piperazinyl]-6,7-dimethoxy-4-quinazolinamine to near reflux and adding slightly more than one equivalent of concentrated aqueous hydrochloric acid. Solution occurred immediately, and the solution was allowed to cool to room temperature and stand for several hours. The precipitate which formed was collected by filtration, washed with ethanol, and dried to yield R(+)-2-[4-[(tetrahydro-2-furanyl)carbonyl]-1-piperazinyl]-6,7-dimethoxy-4-quinazolinamine, hydrochloride salt dihydrate having a melting point of 260.5°–263.5° C. and an optical rotation $[\alpha]_D^{28.5°\ C.} = 23.9°$ (C=1, water).

EXAMPLE 7

Preparation of
S(−)-2-[4-[(tetrahydro-2-furanyl)carbonyl]-1-piperazinyl]-6,7-dimethoxy-4-quinazolinamine Step 1—Preparation of S(−)-tetrahyduroic acid Using the procedure detailed in *Can. J. Chem.*, 61:1383–1386 (1983), racemic tetrahydro-2-furoic acid was first converted to a mixture of the diastereomeric ephedrine salts by reaction with (+)-ephedrine in ethyl acetate. The crude S(−)-ephedrine salt which first precipitated had a melting point of 114°–115° C. The material was recrystallized four times from ethyl acetate to yield material melting at 115°– 117° C. and having an optical rotation $[\alpha]_D^{26.5°\ C.} = +13.4°$ (C=1, methanol) (literature $[\alpha]_D = +13.8°$).

The salt was acidified to recover the S(−)-tetrahydro-2-furoic acid, b.p. 60° C. at 0.5 mm Hg, refractive index, $\eta_D^{25} = 1.4582$, optical rotation $[\alpha]_D^{22} = -32.02°$ (C=1, chloroform) (literature $[\alpha]_D = -30.1°$ (C=1, chloroform)).

Step 2—Preparation of
S(−)-2-[4-[(tetrahydro-2-furanyl)carbonyl]-1-piperazinyl]-6,7-dimethoxy-4-quinazolinamine The procedure employed was the same as that described above in Example 5 for the R(+)-enantiomer, yielding S(−)-2-[4-[(tetrahydro-2-furanyl)carbonyl]-1-piperazinyl]-6,7-dimethoxy-4-quinazolinamine, m.p. 269.5°–271.1° C., optical rotation $[\alpha]_D^{22°\ C.} = -26.9°$ (C=1, 3N hydrochloric acid).

EXAMPLE 8

Preparation of
S(−)-2-[4-[(tetrahydro-2-furanyl)carbonyl]-1-piperazinyl]-6,7-dimethoxy-4-quinazolinamine,
hydrochloride salt The procedure employed was the same as in Example 6 for the preparation of the hydrochloride salt of the R(+)-enantiomer. M.p. 271.5°–273° C. (dec.), optical rotation $[\alpha]_D^{28.5°\ C.} = -23.1°$ (C=1, water).

The foregoing description and the EXAMPLES are merely illustrative and are not intended to limit the invention to the disclosed embodiments. Variations and changes which are obvious to one skilled in the art are intended to be within the scope and nature of the invention which are defined in the appended claims.

What is claimed is:

1. A sustained-release drug dosage form comprising (1) granules of a drug which is terazosin or a salt or hydrate thereof coated with a sustained-release coating composition comprising from about 2 to about 20 weight percent (w/v) of an ethylcellulose or a methacrylic methylester, from about 0.1 to abut 5.0 weight percent (w/v) of a plasticizer and from about 0.5 to about 20 weight percent (w/v) of a detackifying agent and (2) a slow release matrix comprising at least one viscosity agent.

2. The drug dosage form of claim 1 wherein said plasticizer is selected from the group consisting of castor oil, propylene glycol, polyethylene glycol, acetyl triethyl citrate, acetyl tributyl citrate, triethyl citrate and tributyl citrate.

3. The drug dosage form of claim 1 wherein said detackifying agent is selected from the group consisting of magnesium stearate, talc, titanium dioxide and silica gel.

4. The drug dosage form of claim 1 wherein the coating composition comprises from about 2 to about 20 weight percent (w/v) of ethylcellulose, from about 0.1 to about 5.0 weight percent (w/v) of castor oil and from about 0.5 to about 20 weight percent (w/v) of magnesium stearate.

5. The drug dosage form of claim 1 wherein said drug is terazosin monohydrochloride dihydrate.

6. The drug dosage form of claim 1 wherein said viscosity agent is selected from the group consisting of methylcellulose, hydroxypropylmethylcellulose, povidone and hydroxypropylcellulose.

7. The dosage form of claim 1 comprising:
   from about 2.0 to about 80 weight percent sustained release coated drug granules;
   from about 0 to about 30 weight percent calcium phosphate;
   from about 2 to about 30 weight percent of a first viscosity agent and from about 0 to about 30 weight percent of a second viscosity agent wherein said first and second viscosity agents are independently selected from the group consisting of methylcellulose, hydroxypropylmethylcellulose, povidone and hydroxypropylcellulose.

8. The dosage form of claim 1 comprising:
   from about 2.6 to about 26.4 weight percent of sustained-release coated terazosin monohydrochloride dihydrate granules;
   about 2.5 weight percent of methylcellulose;
   about 10.5 weight percent of hydroxypropylmethylcellulose;
   about 34.0 weight percent of calcium phosphate;
   about 1.1 weight percent of stearic acid; and
   about 1.9 weight percent of talc.

9. The drug dosage form of claim 1 wherein said drug is R-(+)-terazosin monohydrochloride dihydrate.

* * * * *